United States Patent [19]
Kwan et al.

[11] Patent Number: 6,143,537
[45] Date of Patent: *Nov. 7, 2000

[54] METHOD FOR STABILIZING ANALYTE STRUCTURE USING ANTIBODIES OR ANTIBODY FRAGMENTS THEREOF

[75] Inventors: Shing F. Kwan, Lake Forest; Ivan E. Modrovich, Camarillo; Rebecca J. Hunt, Carpinteria, all of Calif.

[73] Assignee: Medical Analysis Systems, Inc., Camarillo, Calif.

[ * ] Notice: This patent is subject to a terminal disclaimer.

[21] Appl. No.: 09/225,905

[22] Filed: Jan. 5, 1999

Related U.S. Application Data

[63] Continuation of application No. 07/956,838, Oct. 5, 1992, which is a continuation of application No. 07/382,425, Jul. 19, 1989, abandoned.

[51] Int. Cl.[7] ............ G01N 33/53; G01N 33/573; C12Q 1/37; C12Q 1/32; C12Q 9/96
[52] U.S. Cl. ............ 435/188; 435/7.1; 435/7.4; 435/7.7; 435/7.71; 435/7.92; 435/23; 435/24; 435/26; 435/27; 435/28; 435/188; 436/8; 436/16; 436/18; 436/176; 436/512; 436/826; 524/900
[58] Field of Search .................... 435/7.1, 7.4, 7.7, 435/7.71, 7.92, 23, 24, 26, 27, 28, 188; 524/900; 436/8, 16, 18, 176, 512, 826

[56] References Cited

U.S. PATENT DOCUMENTS

| | | |
|---|---|---|
| 4,157,280 | 6/1979 | Halbert et al. . |
| 4,267,272 | 5/1981 | Josephson ............ 435/7 |
| 4,585,754 | 4/1986 | Meisner et al. . |
| 4,652,524 | 3/1987 | Modrovich et al. ........ 435/188 |
| 4,670,258 | 6/1987 | Harris et al. . |
| 5,660,978 | 8/1997 | Kwan et al. ............ 435/5 |
| 5,686,253 | 11/1997 | Skold et al. ............ 435/7.9 |
| 5,686,579 | 11/1997 | Shami et al. ............ 530/387.3 |

FOREIGN PATENT DOCUMENTS

| | | |
|---|---|---|
| 18652/88 | 4/1988 | Australia . |
| 0 298 654 B1 | 1/1994 | European Pat. Off. . |

OTHER PUBLICATIONS

Shami et al. 1989. Trends in Biotech. 7 (7): 186–190.
Sternberger, et al. "The unlabeled antibody enzyme method of immunohistochemistry," *J. Histochem. Cytochem.* 18: 315–333 (1970).
Sawada, et al. "Human prostatic acid phosphatase (EC–3.1.3.24) Stabilization of prostatic acid phosphatase against thermal inactivation by the homologous antibody," *Chem Pharm Bull* (Tokyo) 29:2935–2939 (1981), abstract only.
Cheridnikova, et al. "Evidence for the stabilizing effect of antibodies on the subunit association of glyceraldehyde–3–phosphate dehydrogenase," *Mol. Immunol.* 18: 1055–1064 (1981), abstract only.
Melchers, et al. "Enhanced stability aganist heat denaturation of *E. coli* type and mutant β–galactosidase in the presence of specific antibodies," *Biochem. Biophys. Res. Comm.* 40:570–575 (1970).
Boyd "*Fundamentals of immunology, Third Edition*" (Interscience Publishers, Inc., New York) pp. 318–326 (1956).
Mason, et al. "Prearation of Peroxidase: Antiperoxidase (PAP) Complexes for Immunohistological labeling of Monoclonal Antibodies," Histochem. Cytochem., 30(11):1114–1122, (1982).
Precitrol–N Control Serum and Diluent 620200; Boehringer Mannheim Catalog (1988).
Foti, et al. "The effect of antibody on human prostatic acid phosphatase. Substrate utilization by enzyme or enzyme–antibody complex," whole abstract(#85:139088h). Chemical Abstracts, 85(19):199 (1976).
P. Tijssen, "Practice and Theory of Enzyme immunoassays," *Laboratory Techniques in Biochemistry and Molecular Biology*, 15:95–121 (1985), Chapter 7.
Ailsa M. Campbell, "Monoclonal Antibody Technology," *Laboratory Techniques in Biochemistry and Molecular Biology*, 13:1–33 (1984), Chapter 1.
Hideo Fukui, et al., Japanese Patent Application No. 58–081782, Preservation of Beta–galactosidase (complex) solution—derived from *E. coli* by addition of sugar, gelatin or glycerol prevents loss of due to freezing (Abstract Only), May 17, 1983, Mitsui Toatsu Chem. Inc. K.K. (Applicant).
Tsuneo Hanyu, Japanese Patent Application No. 59–210885, Stable peroxidase enzyme preparation—contains peroxidase, polyalkylene glycol and serum protein treated with halogenated hydrocarbon (Abstract Only), Nov. 29, 1984, Toyobo K.K. (Applicant).
Ramjeesing, et al., 1138461, Siologically active complex with enhanced resistance to inactivation—formed from molecule having biological activity and antibody recognizing molecule (Abstract Only), May 31, 1989, Hybrisens LTD (Applicant).

*Primary Examiner*—James C. Housel
*Assistant Examiner*—Ja-Na A. Hines
*Attorney, Agent, or Firm*—Morrison & Foerster, LLP

[57] ABSTRACT

A method for stabilizing analyses with antibodies and antibody fragments comprises dissolving the analyte in a liquid to form a solution, adding analyte-specific antibodies, fragments of such antibodies, or both to the solution, heating the solution, and then cooling and filtering the solution. The filtered solution may be diluted in a suitable matrix.

45 Claims, No Drawings

METHOD FOR STABILIZING ANALYTE STRUCTURE USING ANTIBODIES OR ANTIBODY FRAGMENTS THEREOF

CROSS REFERENCE TO RELATED APPLICATIONS

This is a continuation of application Ser. No. 07/956,838, filed Oct. 5, 1992, which is a continuation of Ser. No. 07/382,425, filed Jul. 19, 1989, now abandoned.

BACKGROUND OF THE INVENTION

The physiological activity of many macromolecular biomolecules depends upon their tertiary and secondary structures, as well as their primary structures. Molecules with fibrous, globular, and other structures are known. Deconvolution of conformational features of a macromolecule (e.g., an enzyme) can significantly reduce or even destroy the molecule's activity. Changes in the tertiary structure of a macromolecule can be caused by heat, strong acids or bases, and other conditions.

The use of enzymes, hormones, and other biomolecules in both clinical and research capacities is well established. Such compounds are often difficult to isolate and expensive to manufacture. It is desirable to protect these and other analytes from denaturation, degradation, and other processes that destroy physiological activity.

The medical and research communities have exploited the interaction between antibodies and antigens for a variety of detection methodologies for over 30 years. Common techniques include tissue staining, radioimmunoassaying, enzyme immunoassaying, fluorescence immunoassaying, and immunoelectrophoresis. In each case, the unique ability of an antibody to bind specifically to a particular antigen is exploited.

An antibody may be broadly defined as a globular protein formed in response to the introduction of an antigen. Antibodies have molecular weights of about 160,000, and may be produced by monoclonal and polyclonal techniques.

An antigen may be defined as a substance which reacts with the products of specific humoral or cellular immunity; in other words, antigens are substances that react in a specific manner with antibodies. Numerous types of natural and synthetic antigens are known, including proteins, carbohydrates, nucleic acids, and lipids. Antibodies themselves can act as antigens. Haptens are small molecules that can react with specific antibodies, but do not elicit specific antibody production unless injected in a conjugated form. In other words, the hapten must be conjugated to a high molecular weight carrier such as bovine serum albumin.

An antibody has two functionally distinct regions, called the "variable" region, and the "constant" region, respectively. The variable region can bind to an antigen without the formation of covalent chemical bonds. The constant region can associate with cellular receptors. Differences in the molecular make-up of the constant regions define particular classes and subclasses of immunoglobulins. There are five principal classes, denoted in the art as IgG, IgA, IgM, IgD and IgE, with IgG being the most prevalent.

A given antibody can react only with its homologous antigen, or with an antigen of similar molecular structure. In contrast, a given antigen may interact with more than one type of antibody. A "key-lock" analogy is often used to describe the interaction; the antigen resembles a key which precisely fits an antibody's corresponding structural shape, or "lock." Non-covalent binding stabilizes the complex and holds it together.

The antigen-antibody interaction is primarily a result of three forces: van der Waal's and London forces (dipole-dipole interactions), hydrophobic interactions, and ionic (coulombic) bonding.

SUMMARY OF THE INVENTION

The present invention provides a process for the stabilization of antigens ("analyses" herein) in a liquid medium, utilizing the unique properties of antibodies. The invention thus provides stabilized analyte preparations which have desirable processing characteristics (e.g., the ability to be aseptically filtered). The process comprises binding antibodies or antibody fragments to proteins, enzymes, and other analyses, to prevent the spontaneous folding or unfolding of, e.g., peptide chains within the analyte. Additionally, the bounding antibody or antibody fragment shields the analyte (including enzymes) from proteolytic enzymes and various oxidizing compounds. The antibody-stabilized analyses retain their bioactivity.

In a preferred embodiment of the invention, a stabilized analyte is prepared by adding the analyte in a saline solution, then adding antibodies or antibody fragments to the solution. The solution is preferably agitated and heated, and then cooled and filtered. The filtered solution is then diluted into a defined matrix of desirable concentration. The solution is assayed for antibody-stabilized analyte activity during and after the preparation of the stabilized complex.

DETAILED DESCRIPTION

As used herein, the term "analyte" refers to a macromolecule that can provide or coact with an antigen. Examples include peptides, proteins, glycoproteins, lipoproteins, enzymes, carbohydrates, and nucleic acids. More particularly, the following enzymes are representative of some of the analytes which may be stabilized with the present invention: prosthetic acid phosphatases, aspartate aminotransferases, alanine aminotransferases, amylases, malate dehydrogenase, ureases, hexokinases, glucose-6-phosphate dehydrogenases, peroxidases, creative kineses, glutamate dehydrogenases, and alkaline phosphatases. Hereinafter, "antigen" shall mean antigens and the functional parts of such antigens.

In accordance with the present invention, an analyte is stabilized by first dissolving the analyte in an appropriate solvent. Enzymes, antibodies, and other globular proteins are typically soluble in water or aqueous solutions of acids, bases or salts. Other analyses may be solvated in aqueous or nonaqueous solutions. Preferably a 0.5% to 30% saline solution is used.

Once a solution of the analyte has been prepared, a predetermined amount of antibodies is added to the analyte solution. More than one type of the antibody may be added. The antibodies used in the present invention may be prepared, isolated, and purified by a variety of methods that will be understood by those skilled in the art. Stabilized analyte solutions can be prepared with monoclonal and polyclonal, antibodies. For example, polyclonal antibodies may be produced by injecting the analyte of interest into a host mammal, thereby inducing an antigenic response that results in antibody formation. After bleeding the mammal, standard fractionation procedures are used to isolate various types of antibodies, each of which is specific to the particular analyte. The antibodies so produced can be combined with the analyte to yield a stabilized analyte-antibody complex. Mammals include rats, mice, primates, goats, sheep, rabbits, cows, horses and the like.

After an analyte-antibody solution is prepared, the solution is agitated and heated for a period of time sufficient to allow formation of a stabilized analyte-antibody complex. Depending on the system equilibrium may be reached in seconds, hours, or days. Typically the analyte-antibody solution is heated for several minutes to several hours, at temperatures of ambient to about 65° C. In addition to accelerating the formation of a stabilized analyte-antibody complex, elevated temperatures reduce or even eliminate instable enzymatic activity of the solution.

After a stabilizing amount of time has passed, the analyte-antibody solution may then be cooled, filtered, and assayed for analyte content. Filtration may be accomplished by passing the equilibrated solution through a suitable size control device, such as a filter, molecular sieves, resins, hollow fibers, and spiral cartridge exclusions. Preferably, a 0.2 micron aseptic filter is used. If desired, the filtered solution may be diluted by adding the solution to a matrix which may be a chemical reagent, a buffered solution, a salt solution, protein solution, polymer solutions and mixtures thereof. A presently preferred protein matrix solution essentially consists of a stabilized preparation of mammalian serum, such as human, bovine, equine, porcine, rabbit serum and the like components, or mixtures thereof. The antibody-stabilized analyte is used to adjust the activity by diluting into protein matrix as desired. The protein solution may be heated, cooled and filtered as desired.

It has been found that certain analytes tend to form insoluble immunocomplexes when allowed to react with whole antibody molecules, in part because of the generally divalent nature of most antibodies. Immunocomplexes have extremely high molecular weights, may be insoluble, and may be unsuited for processing techniques such as aseptic filtration.

Accordingly, in a preferred embodiment of the invention, antibody Fab fragments or mixtures of whole antibodies and Fab fragments are added to the analyte solution. Because Fab antibody fragments are monovalent, formation of insoluble immunocomplexes is avoided and the benefits of stabilization and filterability are achieved.

The fragmentation of antibodies may be accomplished in a number of ways.[1] A preferred method is papain hydrolysis using enzymes such as papain. Papain (also called papayotin) is an enzyme with substantial thermos/ability. It is capable of "digesting" or fragmenting protein molecules. Treatment of an antibody with papain in an aqueous medium yields three antibody fragments: two "Fab" fragments and one "Fc" fragment. Fc denotes a fragment which includes the "constant" region of the molecule.

[1] "Handbook of Experimental Immunology," Stanworth and Turner, D. W. Weir 2nd Ed. 1973, Blackwell Scientific Publication, Oxford (incorporated herein by reference).

Each Fab fragment possesses one antigen-combining site (the "variable" region), and may combine with an antigen in a manner similar to a whole molecule antibody. In contrast, the Fc fragment often lacks antigen-binding capability, but retains many antigenic and biological properties of the parent antibody.

EXAMPLE 1

Preparation of Stabilized Human Prosthetic Acid Phosphatase (ACP)

Stabilized ACP was prepared as follows:

ACP was added to 10 ml of 0.9% NaCl at 4° C. to yield an ACP concentration of 877 IU. 6 mg of Fab was added to the solution. Here, "Fab" denotes antibody fragments the solution. Here, "Fab" denotes antibody fragments formed by papain hydrolysis of various polyclonal antibodies. The antibodies were formed in response to an ACP-induced antigenic response in a host mammal.

The solution was rocked at room temperature for four hours. 4.8 mg of IgG was then added to the solution. Here, "IgG" denotes whole molecule polyclonal antibodies prepared as described above.

The solution was rocked overnight at room temperature, then heated for 36 minutes at 56° C.

The solution was cooled at 4° C., and filtered through a 0.2 micron filter.

The filter solution was assayed for ACP, using conventional techniques.

The filtered solution was diluted by adding a protein matrix, heated at 57° C. for 30 minutes, and then cooled to 4° C.

The solution was again filtered through a 0.2 micron filter.

Enzymatic activity of stabilized ACP prepared in the above manner is shown in Table 1. The stability studies were conducted at different temperatures. The results show that enzymatic activity remained high even after three days at elevated temperatures. The control solution had an ACP concentration of 1.00 IU at time O at 4° C.

TABLE 1

Accelerated Stability of Stabilized ACP

| Pilot | Activity of ACP (in IU) after solutions were stored at 72 hours at temperature shown | | |
|---|---|---|---|
|  | 4° C. | 41° C. | 47° C. |
| Stabilized | 1.23 | 1.32 | 1.00 |
| Control Untreated | 0.20 | 0 | 0 |

The results of long term stability studies, carried out at lower temperatures, are shown in Table 2. ACP activity remained even after 71 days. "RT" denotes room temperature.

TABLE 2

Accelerated Stability of Stabilized ACP

| Storage time in day/ Storage Temp |  | 6 | 13 | 27 | 41 | 56 | 71 |
|---|---|---|---|---|---|---|---|
| Stabilized | 4° C. | 1.69 | 1.79 | NA | 1.94 | NA | 1.88 |
|  | R.T. | 1.84 | 1.92 | 1.78 | 2.00 | 1.96 | 1.94 |
| Untreated | R.T. | 0 | NA | NA | NA | NA | NA |

EXAMPLE 2

Preparation of Stabilized Calf Intestine Alkaline Phosphatase (ALP)

Stabilized ALP was prepared as follows:

ALP was added to a 0.9% NaCl solution to yield an ALP concentration of 18500 IU.

120 mg of Fab was added to 12 ml of the above solution, and the resulting solution was rocked for two hours at room temperature. The Fab was prepared by papain hydrolysis of ALP-induced polyclonal antibodies.

25 mg of IgG was added to the mixture. Here, IgG denotes whole molecule polyclonal antibodies prepared in response to an ALP-induced antigenic response in a host animal.

The mixture was rocked overnight at room temperature.

The mixture was heated at 57° C. for 35 minutes, then cooled to 4° C. and filtered through a 0.2 micron filter.

After assaying for ALP, the filtered solution was diluted to a desirable concentration by adding it to a protein matrix, heated at 57° C. for 30 minutes, and cooled to 4° C.

The stabilized solution was then filtered through a 0.22 micron filter.

The results of short-term (accelerated conditions) and long-term stability studies of stabilized ALP are shown in Tables 3 and 4 respectively.

TABLE 3

Accelerated Stability of Stabilized ALP

| | Activity of ALP (in IU) after solutions were stored for 6 days at temperature shown | | |
|---|---|---|---|
| | 4° C. | 41° C. | 47° C. |
| Stabilized | 482 | 464 | 437 |
| Untreated | 450 | 135 | 68 |

TABLE 4

Long-Term Stability of Stabilized ALP

| Storage time in day/ Storage Temp | | 6 | 13 | 27 | 41 | 56 | 71 |
|---|---|---|---|---|---|---|---|
| Stabilized | 4° C. | 374 | 384 | NA | 387 | NA | 387 |
| | R.T. | 370 | 381 | 372 | 380 | 385 | 383 |
| Untreated | R.T. | 200 | 100 | NA | NA | NA | NA |

Stabilization of analytes in the manner described above yields preparations which resist denaturing and degrading conditions, and which retain their bioactivity for a substantial period of time.

It will be appreciated by those skilled in the art that a number of additional modifications and improvements can be made to the invention without departing from its essential spirit and scope. Accordingly, the above disclosure does not limit the invention, which is limited only by the following claims.

What is claimed is:

1. A method for increasing the stability of a protein analyte susceptible to degradation in a liquid solution upon storage, comprising:
   (a) preparing a liquid solution containing the protein analyte;
   (b) adding a stabilizing amount of a stabilizing antibody to the solution containing the analyte, wherein the stabilizing antibody has binding specificity for the analyte in the liquid solution; and
   (c) incubating the solution containing the protein analyte and the stabilizing antibody under conditions sufficient to allow the antibody to bind to the protein analyte to form an antibody-analyte complex, wherein the protein analyte in the solution with the stabilizing antibody is stable for at least 72 hours at 4° C.

2. The method of claim 1, wherein the antibody is a polyclonal antibody.

3. The method of claim 1, wherein the antibody is a monoclonal antibody.

4. The method of claim 1, wherein the antibody includes both polyclonal and monoclonal antibody.

5. The method of claim 1, wherein the antibody is a whole antibody.

6. The method of claim 1, wherein the antibody is in the form of monovalent fragments of antibody.

7. The method of claim 6, wherein the monovalent fragments of antibody also include whole antibody.

8. The method of claim 7, wherein the monovalent fragments of antibody are added to the solution containing the protein analyte and the whole antibody is added later.

9. The method of claim 6, wherein the monovalent fragments are Fab fragments produced by digestion with papain.

10. The method of claim 1, further comprising sterile filtering the antibody-analyte complex.

11. The method of claim 1, wherein the analyte is stable after treatment at 41° C. for 72 hours.

12. The method of claim 1, wherein the protein analyte is an enzyme selected from the group consisting of prostatic acid phosphatase, aminotransferase, amalyse, malate dehydrogenase, urease, hexokinase, glucose-6-phosphate dehydrogenase, peroxidase, creatine kinase, glutamate dehydrogenase, and alkaline phosphatase.

13. A method for increasing the stability of a protein analyte susceptible to degradation in a liquid solution upon storage, comprising:
   (a) preparing a liquid solution containing the protein analyte;
   (b) adding a stabilizing amount of a stabilizing antibody to the solution containing the protein analyte, wherein the stabilizing antibody has binding specificity for the analyte in the liquid solution and wherein the stabilizing antibody includes both whole antibody and monovalent binding fragments of antibody; and
   (c) incubating the solution containing the protein analyte and the stabilizing antibody under conditions sufficient to allow the antibody to bind to the analyte to form an antibody-analyte complex, whereby the antibody increases the stability of the protein analyte to degradation in the liquid solution upon storage.

14. The method of claim 13, wherein the antibody is a polyclonal antibody.

15. The method of claim 13, wherein the antibody is a monoclonal antibody.

16. The method of claim 13, wherein the monovalent fragments are Fab fragments produced by digestion with papain.

17. The method of claim 13, wherein the monovalent fragments of antibody are added to the solution containing analyte and the whole antibody is added later.

18. The method of claim 13, further comprising sterile filtering the antibody-analyte complex.

19. The method of claim 13, wherein the analyte is stable after treatment at 41° C. for 72 hours.

20. The method of claim 13, wherein the analyte is stable after treatment at 4° C. for 72 hours.

21. The method of claim 13, wherein the protein analye is an enzyme selected from the group consisting of prostatic acid phosphatase, aminotransferase, amalyse, malate dehydrogenase, urease, hexokinase, glucose-6-phosphatase dehydrogenase, peroxidase, creatine kinase, glutamate dehydrogenase, and alkaline phosphatase.

22. A method for preparing a sterile liquid solution containing a protein analyte wherein the analyte has increased stability to degradation upon storage, comprising:
   (a) preparing a liquid solution containing the protein analyte;
   (b) adding a stabilizing amount of a stabilizing antibody to the solution containing the protein analyte, wherein the stabilizing antibody has binding specificity for the analyte in the liquid solution;

(c) incubating the solution containing analyte and stabilizing antibody under conditions sufficient to allow the antibody to bind to the protein analyte to form an antibody-analyte suitable for aseptic filtration; and (d) aseptically filtering the incubated solution containing antibody-analyte complex; whereby a sterile liquid solution of a protein analyte with increased stability to degradation in a liquid solution upon storage is prepared.

23. The method of claim 22, wherein the antibody is a polyclonal antibody.

24. The method of claim 22, wherein the antibody is a monoclonal antibody.

25. The method of claim 22, wherein the antibody includes both a polyclonal and a monoclonal antibody.

26. The method of claim 22, wherein the antibody is a whole antibody.

27. The method of claim 22, wherein the antibody is in the form of monovalent fragments.

28. The method of claim 27, wherein the monovalent fragments of the antibody also include a whole antibody.

29. The method of claim 28, wherein the monovalent fragments of the antibody are added to the solution containing analyte and the whole antibody is added later.

30. The method of claim 28, wherein the monovalent fragments are Fab fragments produced by digestion with papain.

31. The method of claim 22, wherein the anlalyte is stable after treatment at 41° C. for 72 hours.

32. The method of claim 22, wherein the analyte is stable after treatment at 4° C. for 72 hours.

33. The method of claim 22, wherein the protein analyte is an enzyme selected from the group consisting of prostatic acid phosphatase, aminotransferase, amalyses, malate dehydrogenase, urease, hexokinase, glucose-6-phosphate dehydrogenase, peroxidase, creatine kinase, glutamate dehydrogenase, and alkaline phosphatase.

34. A method for stabilizing a biological activity of a protein analyte in a liquid solution upon storage, comprising:

(a) preparing a liquid solution containing the protein analyte, wherein the protein analyte exhibits the biological activity in solution;

(b) adding a stabilizing amount of a stabilizing antibody to the solution containing the analyte, wherein the stabilizing antibody has binding specificity for the analyte in the liquid solution; and (c) incubating the solution containing analyte and stabilizing antibody under conditions sufficient to allow the antibody to bind to the analyte to form an antibody-analyte complex, and wherein the biological activity of the protein analyte is stable upon binding of the antibody and the analyte in the solution with stabilizing antibody is stable for at least 72 hours at 4° C.

35. The method of claim 34, wherein the antibody is a polyclonal antibody.

36. The method of claim 34, wherein the antibody is a monoclonal antibody.

37. The method of claim 34, wherein the antibody includes both a polyclonal and a monoclonal antibody.

38. The method of claim 34, wherein the antibody is a whole antibody.

39. The method of claim 34, wherein the antibody is in the form of monovalent fragments.

40. The method of claim 39, wherein the monovalent fragments of the antibody also include a whole antibody.

41. The method of claim 40, wherein the monovalent fragments of the antibody are added to the solution containing analyte and the whole antibody is added later.

42. The method of claim 39, wherein the monovalent fragments of the antibody are Fab fragments produced by digestion with papain.

43. The method of claim 34, further comprising sterile filtering the antibody-analyte complex.

44. The method of claim 34, herein the analyte is stable after treatment at 41° C. for 72 hours.

45. The method of claim 34, wherein the protein analyte is an enzyme selected from the group consisting of prostatic acid phosphatase, aminotransferase, amalyse, malate dehydrogenase, urease, hexokinase, glucose-6-phosphate dehydrogenase, peroxidase, creatine kinase, glutamate dehydrogenase, and alkaline phosphatase.

\* \* \* \* \*